United States Patent [19]
Osborn, III

[11] Patent Number: 6,096,017
[45] Date of Patent: *Aug. 1, 2000

[54] EXTENSIBLE ABSORBENT ARTICLES HAVING LESS EXTENSIBLE BARRIERS

[75] Inventor: Thomas Ward Osborn, III, Cincinnati, Ohio

[73] Assignee: The Procter & Gamble Company, Cincinnati, Ohio

[*] Notice: Under 35 U.S.C. 154(b), the term of this patent shall be extended for 915 days.

[21] Appl. No.: 08/506,137

[22] Filed: Jul. 24, 1995

Related U.S. Application Data

[63] Continuation of application No. 08/342,678, Nov. 21, 1994, abandoned, which is a continuation of application No. 08/096,534, Jul. 22, 1993, abandoned, which is a continuation-in-part of application No. 08/073,256, Jun. 7, 1993, Pat. No. 5,389,094, which is a continuation of application No. 07/769,891, Oct. 1, 1991, abandoned.

[51] Int. Cl.$^7$ ................................................ A61F 13/15
[52] U.S. Cl. ................ 604/385.07; 604/385.16; 604/385.21; 604/385.22; 604/385.23; 604/385.28; 604/387
[58] Field of Search .................. 604/378–391, 604/393–396

[56] References Cited

U.S. PATENT DOCUMENTS

| | | | |
|---|---|---|---|
| Re. 30,057 | 7/1979 | Schaar | 604/378 |
| 3,776,233 | 12/1973 | Schaar | 604/385.1 |
| 3,807,402 | 4/1974 | Miller | 604/378 |
| 3,848,599 | 11/1974 | Schaar | 604/385.1 |
| 3,885,568 | 5/1975 | Schaar | 604/385.1 |
| 3,978,861 | 9/1976 | Schaar | 604/378 |
| 3,995,640 | 12/1976 | Schaar | 604/378 |
| 4,036,233 | 7/1977 | Kozak | 604/385.2 |
| 4,758,241 | 7/1988 | Papajohn | 604/387 |
| 4,938,755 | 7/1990 | Foreman | 604/385.2 |
| 5,026,364 | 6/1991 | Robertson | 604/385.2 |

FOREIGN PATENT DOCUMENTS

| | | | |
|---|---|---|---|
| 2233235 | 1/1991 | United Kingdom | 604/385.1 |
| 9207536 | 5/1992 | WIPO | 604/387 |
| 9306805 | 4/1993 | WIPO | 604/387 |

*Primary Examiner*—John G. Weiss
*Assistant Examiner*—Karin M. Reichle
*Attorney, Agent, or Firm*—Matthew P. Fitzpatrick; Jeffrey V. Bamber

[57] ABSTRACT

The present invention relates to absorbent articles such as sanitary napkins, panty liners, and incontinence pads. More particularly, the present invention relates to extensible absorbent articles, such as sanitary napkins, that are provided with less extensible lips that serve as barriers to the flow of liquids. When the absorbent article is extended, the less extensible barriers move to a more upright disposition.

11 Claims, 4 Drawing Sheets

| | LONGITUDINAL | | | WIDTH | | | FORCE WALL | |
|---|---|---|---|---|---|---|---|---|
| | % LONGITUDINAL STRETCH | g. OF FORCE TO EXTEND PAD | % PAD SET | % WIDTH STRETCH | g. OF FORCE TO EXTEND 1.0" STRIP | % PAD SET | % STRETCH | g. FORCE |
| CONDITIONS FOR STRETCH | 40% | ≤1000 g. ≤800 g. | ≤10 ≤10 ≤25 | 40% | ≤500 g. ≤400 g. | ≤10 ≤25 | 50% | 1500 g. 2000 g. 2500 g. |
| | 25% | ≤800 g. ≤400 g. ≤300 g. | ≤10 ≤25 | 25% | ≤500 g. ≤400 g. | ≤10 ≤25 | 40% | 1500 g. 2000 g. 2500 g. |
| MINIMUM FORCE TO STRETCH | 25% | ≥50 g. | | | | | 25% | 1500 g. 2000 g. 2500 g. |

Fig. 7

EXTENSIBLE ABSORBENT ARTICLES HAVING LESS EXTENSIBLE BARRIERS

CROSS-REFERENCE TO RELATED APPLICATIONS

This is a continuation of U.S. patent application Ser. No. 08/342,678, filed on Nov. 21, 1994, abandoned, which is a continuation of U.S. patent application Ser. No. 08/096,534, filed on Jul. 22, 1993, abandoned, which is a continuation-in-part of the following U.S. patent applications Ser. No. 08/073,256 filed Jun. 7, 1993, now U.S. Pat. No. 5,389,094, which is a continuation of Ser. No. 07/769,891 filed Oct. 1, 1991, abandoned.

FIELD OF THE INVENTION

The present invention relates to absorbent articles such as diapers, sanitary napkins, panty liners, and incontinence pads. More particularly, the present invention relates to absorbent articles, such as sanitary napkins, that are extensible which are provided with less extensible lips that serve as barriers to the flow of liquids.

BACKGROUND OF THE INVENTION

Absorbent articles such as sanitary napkins, pantiliners, and incontinence pads are devices that are typically worn in the crotch region of an undergarment. These devices are designed to absorb and retain liquid and other discharges from the human body and to prevent body and clothing soiling. Improving the performance of such absorbent articles, particularly the leakage performance of the same, continues to be a formidable undertaking, although a number of improvements have been made in both their materials and structures.

For instance, disposable absorbent articles have previously been provided with elastic members to improve the side leakage performance of such products. For example, U.S. Pat. No. 3,860,003, issued to Buell on Jan. 14, 1975, discloses elasticized disposable absorbent articles wherein an elastic member is positioned in the side flap of the product between the topsheet and the backsheet. The side flap is gathered by the elastic member such that a boat-like configuration for the pad is presented and the side flaps form a barrier along the edges of the product.

U.S. Pat. No. 4,738,677 issued to Foreman entitled "Absorbent Article Having A Containment Pocket", discloses another type of barrier to the flow of liquids which comprises a first set of barrier cuffs along the longitudinal edges of the absorbent article and a second set of barrier cuffs along the end edges of the absorbent article. The barrier cuffs overlap at corner points to form a containment pocket. The first set of barrier cuffs are provided with a spacing means, such as an elastic member, which spaces both sets of barrier cuffs away from the liquid-receiving surface of the absorbent article.

Typically, most of the disposable absorbent articles of the types mentioned above (that is, sanitary napkins, panty liners, and incontinence pads) are made of materials that will not stretch. That is, the materials (and the article itself) will not stretch under the forces that the absorbent article is normally subjected to when worn. Recently, however, efforts have been directed toward providing extensible absorbent articles for improved comfort and conformity with the wearer's body and undergarments (if the article is of a type worn in an undergarment). PCT Application Publication No. 93/01785 and its corresponding U.S. application Ser. No. 07/915,133, both filed Jul. 23, 1992 (of which the present application is a continuation-in-part), discloses extensible absorbent articles. The search for improvements to the features of such absorbent articles has, however, continued.

In particular, a need exists for an extensible absorbent article, such as a sanitary napkin, that is provided with barriers to the flow of liquids.

It is, therefore, an object of the present invention to provide an extensible absorbent article, such as a sanitary napkin, that is provided with barriers to the flow of liquids.

It is another object of the present invention to provide an extensible absorbent article, such as a sanitary napkin, that is provided with barriers that are less extensible than the sanitary napkin and will change from a relatively flat disposition to a more upright disposition when the sanitary napkin is extended.

These and other objects of the present invention will be more readily apparent when considered in reference to the following description and when taken in conjunction with the accompanying drawings.

SUMMARY OF THE INVENTION

The present invention provides an absorbent article, such as a sanitary napkin. The sanitary napkin of the present invention has at least some extensible components. The sanitary napkin is provided with less extensible barriers to the flow of liquids.

The sanitary napkin has a first end region, a second end region, a central region disposed between the first and second end regions, and a pair of longitudinal side edges and a pair of end edges which form the perimeter of the sanitary napkin. The sanitary napkin, in a preferred embodiment, has a central region that is narrower than the first and second end regions (for example, the sanitary napkin may be hourglass-shaped or dog bone shaped). The sanitary napkin preferably comprises an extensible liquid pervious topsheet; an extensible liquid impervious backsheet joined to the topsheet; an extensible absorbent core positioned between the topsheet and the backsheet; and less extensible liquid impervious lips that serve as barriers to the flow of liquids. In this preferred embodiment, the lips comprise narrow strips of film that overlay the topsheet along the longitudinal side edges of the sanitary napkin. The strips each have inner edges, outer edges, and a pair of ends. The outer edges are disposed farther away from the longitudinal centerline of the sanitary napkin than the inner edges. The outer edges and ends of the strips are secured to the topsheet along the perimeter of the sanitary napkin. The inner edges of the strips are unsecured to the topsheet between the ends.

If the sanitary napkin is unstretched, the strips lay flat against the topsheet. When the sanitary napkin is stretched, the unattached portions of the strips change from a flat disposition to a more upright disposition. The strips form inwardly-facing lips (or gaskets) along the longitudinal edges of the sanitary napkin which serve as barriers to the flow of liquids across the topsheet. The raising of the strips is due to the stretchability differential associated with the attached and unattached edges of the barrier strips. The effect is particularly pronounced when the sanitary napkin has an hourglass or dog bone shape where the central region of the sanitary napkin is narrower than the edge regions. In a particularly preferred embodiment, similar strips can also be affixed along the end edges of the sanitary napkin to form barriers along the entire perimeter of the sanitary napkin.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings (which are not necessarily to scale) in which:

FIG. 7 denotes preferred relationships between the magnitude of stretching forces applied to the sanitary napkin and the amount the sanitary napkin stretches in response to such forces.

DETAILED DESCRIPTION OF THE INVENTION

Figure 1:
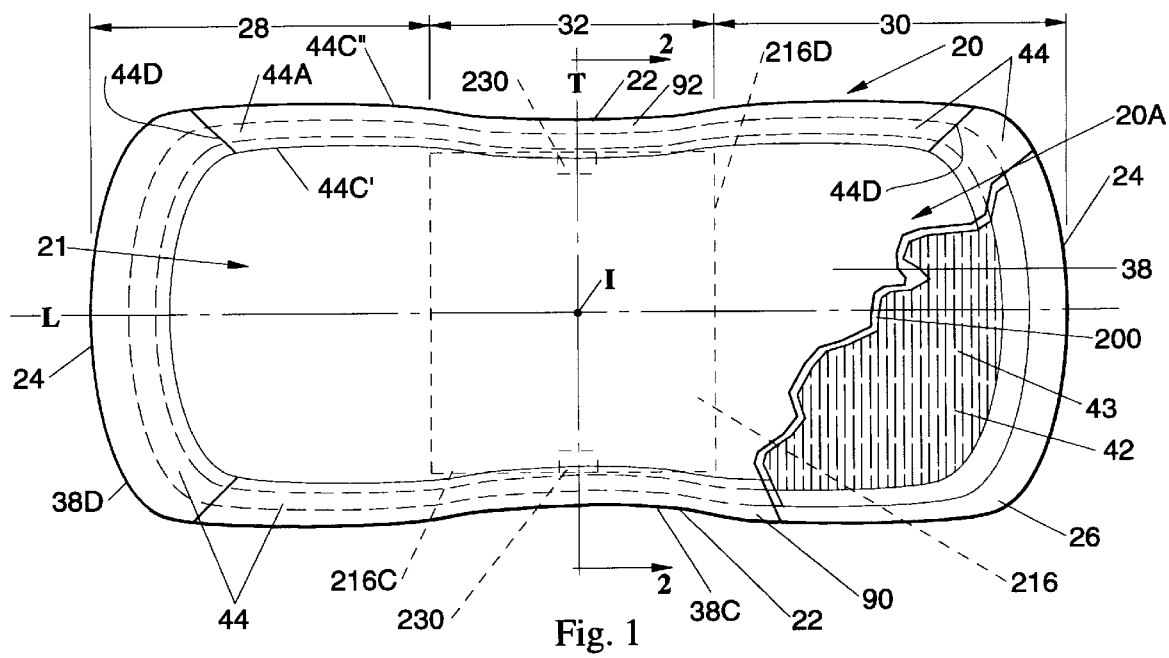
FIG. 1 is a top plan view of a preferred embodiment of the sanitary napkin of the present invention with a portion of the topsheet cut away to show the underlying structure.
Figure 2:
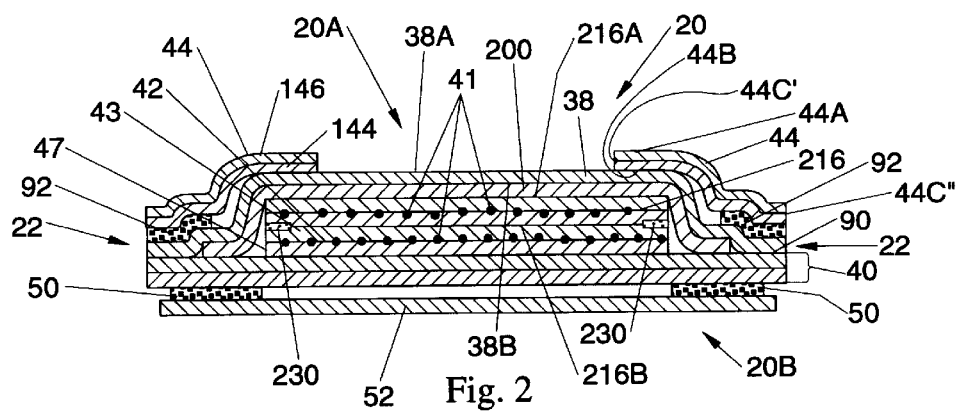
FIG. 2 is a cross sectional view of the sanitary napkin taken along line 2—2 of FIG. 1 (with the size of the barriers greatly enlarged for purposes of illustration).
Figure 3:
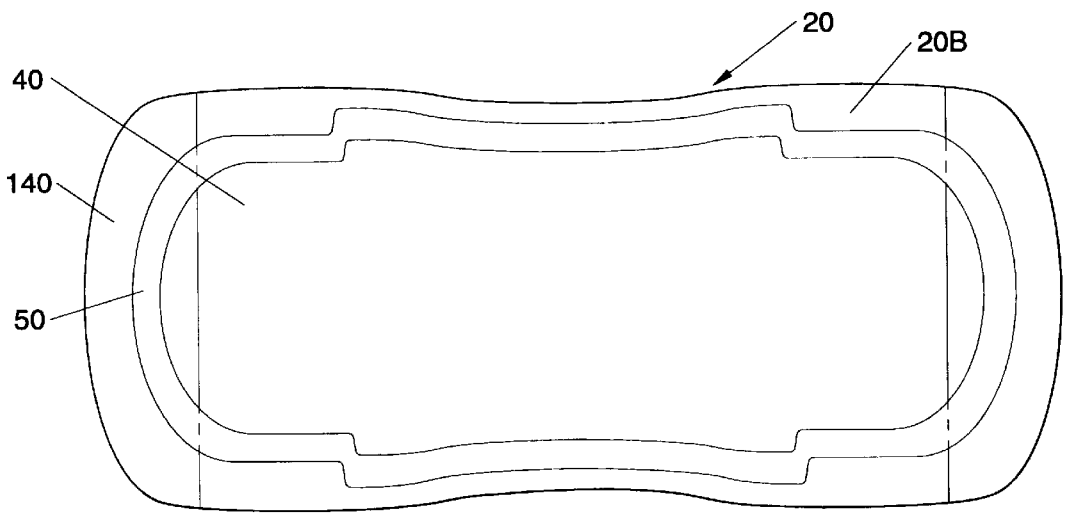
FIG. 3 is a bottom plan view of the sanitary napkin shown in FIG. 1.

FIGS. 1–3 show a preferred embodiment of a disposable absorbent article of the present invention. The present invention relates to extensible absorbent articles, such as diapers, sanitary napkins, panty liners, and incontinence pads, which are provided with less extensible barriers to the flow of liquids.

In the preferred embodiment illustrated, the absorbent article is a sanitary napkin designated 20. The term "sanitary napkin", as used herein, refers to an article which is worn by females adjacent to the pudendal region that is intended to absorb and contain the various exudates which are discharged from the body (e.g., blood, menses, and urine). It should be understood, however, that the present invention is also applicable to other feminine hygiene or catamenial pads such as panty liners, or other absorbent articles such as incontinence pads, and the like.

The sanitary napkin 20 has two surfaces, a liquid pervious body-contacting surface or "body surface" 20A and a liquid impervious garment surface 20B. The sanitary napkin 20 is shown in FIG. 1 as viewed from its body surface 20A. The body surface 20A is intended to be worn adjacent to the body of the wearer. The garment surface 20B of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline L and a transverse centerline T, which interact at point I. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

FIG. 1 shows that the sanitary napkin 20 also has two spaced apart longitudinal edges (or "side edges") 22 and two spaced apart transverse or end edges (or "ends") 24, which together form the perimeter (or periphery) 26 of the sanitary napkin 20. The sanitary napkin (or the main body portion thereof) also has two end regions, which are designated first end region 28 and second end region 30. A central region 32 is disposed between the end regions 28 and 30. The end regions 28 and 30 extend outwardly from the edges of the central region 32 about ⅛ to about ⅓ of the length of the main body portion. A detailed description of the central region 32 and the two end regions 28 and 30 is contained in U.S. Pat. No. 4,690,680 issued to Higgins on Sep. 1, 1987.

The sanitary napkin 20 can be of any thickness, including relatively thick, relatively thin, or even very thin. The embodiment of the sanitary napkin 20 shown in FIGS. 1–3 of the drawings is intended to be an example of a relatively thin sanitary napkin, preferably an "ultra-thin" sanitary napkin. It should be understood, however, when viewing these figures the number of layers of material shown cause the sanitary napkin 20 to appear much thicker than it actually is. An "ultra-thin" sanitary napkin 20 as described in U.S. Pat. Nos. 4,950,264 and 5,009,653 issued to Osborn preferably has a caliper of less than about 3 millimeters. The thin sanitary napkin 20 shown should also be preferably relatively flexible, so that it is comfortable for the wearer.

FIG. 2 shows the individual components of the sanitary napkin 20 of the present invention. The sanitary napkin 20 shown in FIG. 2 generally comprises at least four primary components. These include a liquid pervious topsheet 38, a liquid impervious backsheet 40, an absorbent core 42 positioned between the topsheet 38 and the backsheet 40, and at least one barrier, and preferably, a pair of barriers 44, to the flow of liquids along the side edges 22 of the sanitary napkin. The preferred embodiment shown in FIGS. 1–3 also comprises a less extensible element 216 located in the central region 32 that deflects in response to stretching (and preferably lifts to provide improved body contact). The sanitary napkin to which the barriers are affixed may be one of those described in PCT Publication Nos. WO 93/01785 and 93/01786, and be comprised of one or more extensible components, and more preferably, is comprised of all extensible components (with the exception of the less extensible element), and has an overall extensibility.

Figure 6:
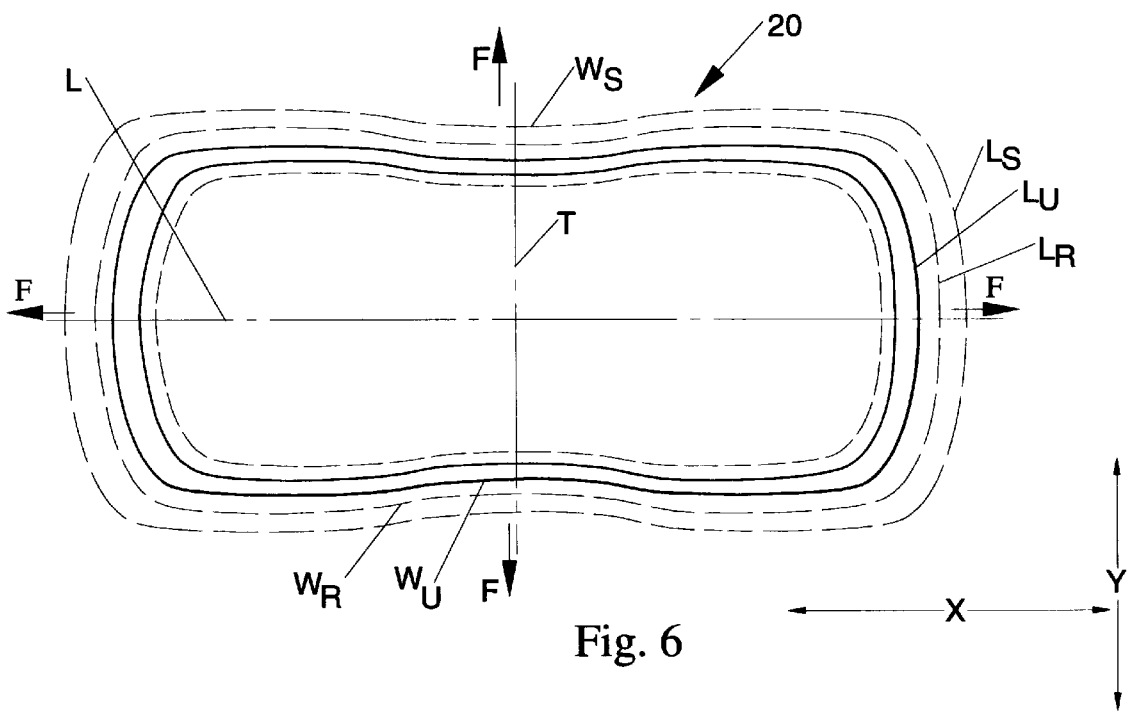
FIG. 6 is a top plan view showing the extensibility of the sanitary napkin (without the barriers for simplicity).

The extensibility of the sanitary napkin 20 is shown in a simplified fashion in FIG. 6. The term "extensible", as used herein refers to articles that can increase in at least one of their dimensions in the x-y plane. The x-y plane is a plane generally parallel to the faces of the sanitary napkin 20. The term extensible includes articles that are stretchable and elastically stretchable (defined below). The sanitary napkin 20 shown in FIG. 6 is preferably extensible both in length and width. The sanitary napkin 20, in other embodiments however, may only be extensible in one of these directions. Preferably, the sanitary napkin 20 is extensible at least in the longitudinal direction.

The sanitary napkin 20 may in some preferred embodiments, in addition to being extensible, also be stretchable. The term "stretchable", as used herein, refers to articles that are extensible when stretching forces are applied to the article and offer some resistance to stretching. More preferably still, the sanitary napkin 20 may be elastically stretchable. The terms "elastically stretchable" or "elastically extensible" are intended to be synonomous. These terms, as used herein, mean that when the stretching forces are removed, the sanitary napkin will tend to return toward its unextended or unstretched (or "original" dimensions) $L_U$ and $W_U$. The sanitary napkin 20 need not return all the way to its unstretched dimensions, however. It may, as shown in FIG. 6, return to relaxed dimensions (such as $L_R$ and $W_R$) between its unstretched dimensions and extended (or stretched dimensions) $L_S$ and $W_S$. Making the sanitary napkin elastically stretchable will reduce the undesirable tendency of the sanitary napkin to gather longitudinally inward (i.e., bunch longitudinally) when forces which tend to stretch the sanitary napkin are removed. This is particularly true when the wearer's panties contract.

The sanitary napkin 20 is preferably extensible in the amounts described in PCT Publication Nos. WO 93/01785 and WO 93/01786. To summarize the same, the sanitary napkin is preferably capable of extending about 5% to less than about 50%, more preferably between about 10% and about 40%, and most preferably between about 25% and about 40% under the forces associated with wearing the sanitary napkin in a pair of panties. Preferably, the sanitary napkin is capable of such extension under forces of between about 50–100 grams to about 1,000–1,500 grams, more preferably under forces of between about 250 grams and about 800 grams. Other preferred amounts of extensibility are set forth in FIG. 7. It is to be understood that all of the limits and ranges specified herein include all narrower ranges, limits, and amounts that are within the specified limits and ranges. The sanitary napkin of the present invention can also be provided with any of the other features of the sanitary napkins described in the above publications including, a structure that provides a "force wall" to prevent elongation past a certain amount without substantial increases in the amount of force applied to the sanitary napkin.

The individual components of the sanitary napkin 20 of the present invention will now be looked at in greater detail with reference to FIGS. 1–3.

The topsheet 38 comprises a first liquid pervious component. When the sanitary napkin 20 is in use, the topsheet 38 is in close proximity to the skin of the user. The topsheet 38 is preferably as compliant, soft feeling, and non-irritating to the user's skin as possible. The topsheet 38 should further exhibit good strikethrough and a reduced tendency to rewet, permitting bodily discharges to rapidly penetrate it and flow toward the core 42, but not allowing such discharges to flow back through the topsheet 38 to the skin of the wearer.

The topsheet 38 has two sides (or faces or surfaces), including a body-facing side 38A and a garment-facing side (or core-facing side) 38B. The body-facing side 38A of the topsheet 38 generally forms at least a portion of the body-contacting surface ("body surface") 20A of the sanitary napkin 20. The topsheet 38 has two longitudinal edges 38C and two end edges 38D.

(A similar numbering system applies to the other components of the sanitary napkin. That is, the side of the component facing the wearer's body can be designated by the number of the component and a reference letter "A". The side facing the wearer's undergarments can be designated by the number of the component and the letter "B". The side and end edges can be designated by the number of the component and the reference letters "C" and "D", respectively.)

A suitable topsheet 38 may be manufactured from a wide range of materials including, but not limited to woven and nonwoven materials, apertured formed thermoplastic films, apertured plastic films, hydro-formed films, porous foams, reticulated foams, reticulated thermoplastic films, and thermoplastic scrims. Suitable woven and nonwoven materials can be comprised of natural fibers (e.g., wood or cotton fibers), synthetic or modified natural fibers (e.g., polymeric fibers, such as polyester, polypropylene fibers, and polyethylene, or polyvinylalcohol, starch base resins, polyurethanes, cellulose esters, nylon, and rayon fibers) or from a combination of natural and synthetic fibers. When the topsheet 38 comprises a nonwoven web, the web may be spunbonded, carded, wet-laid, meltblown, hydroentangled, combinations of the above, or the like.

Apertured films are generally preferred for the topsheet 38 because they are pervious to liquids and, if properly apertured, have a reduced tendency to allow liquids to pass back through and rewet the wearer's skin. Suitable apertured films are described in U.S. Pat. No. 3,929,135 issued to Thompson on Dec. 30, 1975, U.S. Pat. No. 4,324,426 issued to Mullane et al. on Apr. 13, 1982, U.S. Pat. No. 4,342,314 issued to Radel et al. on Aug. 3, 1982, U.S. Pat. No. 4,463,045 issued to Ahr, et al. on Jul. 31, 1984, and U.S. Pat. No. 5,006,394 issued to Baird on Apr. 9, 1991.

The topsheet 38 can be made extensible by performing a mechanical operation, such as pleating, corrugating, or ring rolling on the topsheet material to provide folds in the topsheet that are able to open when the topsheet is stretched. Such a process can be performed on many of the topsheet materials described above. In one preferred embodiment of the present invention, the topsheet 38 is made in accordance with U.S. Pat. No. 4,463,045 and ring rolled to provide it with a degree of longitudinal extensibility. Such a topsheet is described in U.S. patent application Ser. No. 07/936,195 entitled "Polymeric Web Having Deformed Sections Which Provide A Substantially Increased Elasticity To The Web", filed in the name of John J. Curro, et al. on Aug. 25, 1992.

Suitable processes for ring rolling or "pre-corrugating" are described in U.S. Pat. No. 4,107,364 issued to Sisson on Aug. 15, 1978, U.S. Pat. No. 4,834,741 issued to Sabee on May 30, 1989 and in co-pending, commonly assigned U.S. patent application Ser. No. 07/662,536 filed by Gerald M. Weber et al. on Feb. 28, 1991, U.S. patent application Ser. No. 07/662,537 filed by Kenneth B. Buell et al. on Feb. 28, 1991, and U.S. patent application Ser. No. 07/662,543 filed by Gerald M. Weber et al. on Feb. 28, 1991.

The fold lines in the corrugations of a ring rolled topsheet should run in the transverse direction so the topsheet is longitudinally extensible. In other embodiments, the fold lines could run in the longitudinal direction, both directions, and/or other directions. The topsheet 38 will be extensible in directions perpendicular to the fold lines.

In a preferred embodiment, the topsheet 38 is hydrophilic so that liquids will transfer through the topsheet 38 faster than if it was not hydrophilic. This will diminish the likelihood that body exudates will flow off the topsheet rather than being absorbed by the absorbent core. The topsheet can be rendered hydrophilic by treating it with surfactants. Suitable methods of applying surfactants are described in U.S. Pat. Nos. 4,950,254 and 5,009,653 issued to Osborn.

In addition, in preferred embodiments, the inner surface 38B of topsheet 38 is secured in contacting relation with an underlying absorbent layer 200. This contacting relationship results in liquid penetrating topsheet 38 faster than if the topsheet 38 were not in contact with an absorbent component. The topsheet 38 may be kept in a contacting relationship with an underlying layer by bonding the topsheet to the underlying layer. However, it is not absolutely necessary to bond the face of the topsheet 38 to the face of the underlying layer. The topsheet 38 can be maintained in contact with an underlying absorbent component by applying adhesives between the topsheet and the underlying component, by entangling the fibers of the underlying layer with the topsheet, by fusing the topsheet 38 to an underlying absorbent layer by a plurality of discrete individual fusion bonds, or by any means known in the art.

The absorbent core 42 is positioned between the topsheet 38 and the backsheet 40. The absorbent core 42 provides the means for absorbing menses and other body fluids. The absorbent core 42 need not have an absorbent capacity much greater than the total amount of liquid anticipated to be absorbed. The absorbent core 42 is generally compressible, conformable, and non-irritating to the user's skin.

The absorbent core 42 can comprise any material used in the art for such purpose. Non-limiting examples include natural materials such as comminuted wood pulp which is generally referred to as airfelt, creped cellulose wadding, hydrogel-forming polymer gelling agents, modified cross-linked cellulose fibers (such as those described in U.S. Pat. No. 5,217,445 issued to Young, et al. on Jun. 8, 1993), capillary channel fibers (that is, fibers having intra-fiber capillary channels such as those described in U.S. Pat. No. 5,200,248 issued to Thompson, et al. on Apr. 6, 1993), absorbent foams, absorbent sponges, synthetic staple fibers, polymeric fibers, peat moss, or any equivalent material or combinations of materials.

The polymeric gelling agents listed above may also be referred to as "absorbent gelling materials" or "superabsorbent materials". Polymeric gelling agents are those materials which, upon contact with liquids such as water or other body liquids, imbibe such liquids and thereby form hydrogels. In this manner, liquids discharged into the absorbent core 42 can be acquired and held by the polymeric gelling agent, thereby providing the articles herein with enhanced absorbent capacity and/or improved liquid retention performance. The polymeric gelling agent which is employed in the absorbent core 42 will generally comprise particles 41 of a substantially water-insoluble, slightly cross-linked, partially neutralized, hydrogel-forming polymer material. The polymeric gelling agent can be in any form, such as in the form of pellets, flakes, or fibers.

In one preferred embodiment shown in FIG. 2, the absorbent core 42 is a laminate. The laminate is comprised of a layer of superabsorbent polymer material, such as in the form of particles 41, disposed between two air-laid tissues, first and second tissue layers (or "upper" and "lower" tissue layers) 43 and 47, respectively. The first and second tissue layers 43 and 47 provide containment of the superabsorbent polymer material, improve lateral wicking of the absorbed exudates throughout the absorbent core 42 and provide a degree of absorbency. The tissue layers 43 and 47 can be comprised of a single tissue web which is folded with the superabsorbent material particles 41 between, or two separate sheets of the same (or different) tissue.

A suitable laminate is a superabsorbent laminate known as "WATER-LOCK" L-535 available from the Grain Processing Corporation of Muscatine, Iowa ("WATER-LOCK" registered TM by Grain Processing Corporation). Such superabsorbent laminates are disclosed in U.S. Pat. No. 4,467, 012, issued to Pedersen et al. on Aug. 21, 1984, U.S. Pat. No. 4,260,443, issued to Lindsay et al. on Apr. 7, 1981, and U.S. Pat. No. 4,578,068 issued to Kramer, et al. on Mar. 25, 1986.

The laminate absorbent core 42 can be made extensible by cutting or slitting the same. FIG. 1 shows that the absorbent core 42 is a laminate as described above which is slitted (preferably over its entire area) for longitudinal extensibility.

In alternate embodiments, the laminate absorbent core 42 can be made extensible by making the same from tissue paper having between 20% and 200% stretch (i.e., capable of extending to an extended dimension that is between about 1.2 and 3 times its unextended dimension). Such tissue sheets can be made by a number of processes. The tissue paper may in one embodiment, be conventionally creped tissue. For example, the tissue paper may be a "BOUNTY" tissue that is taken directly after it has been creped off of a Yankee dryer before any crepe is pulled out of the tissue. A process for making such a tissue is described in U.S. Pat. No. 5,098,522 issued to Smurkoski, et al. on Mar. 24, 1992.

The longitudinal and end edges 22 and 24 of the sanitary napkin 20 are preferably sealed to prevent the wicking and expulsion of liquid or liquid-containing superabsorbent material from the napkin when it is extended. Alternatively, the edges of the absorbent core 42 may be sealed rather than sealing the edges of the entire sanitary napkin. The edges of the core 42 may, for example, be wrapped or covered by a tissue layer. In other alternative embodiments, the edges of the tissue may be folded, or otherwise manipulated to prevent the wicking and expulsion of liquid or liquid-containing superabsorbent material particles 41 from the core 42. All permanent seals around the perimeter of the sanitary napkin 20 should not break upon lengthening (i.e., any seal is intended to remain for the duration of the use of the sanitary napkin.)

The backsheet 40 prevents the exudates absorbed and contained in the absorbent core 42 from wetting articles which contact the sanitary napkin 20 such as pants, pajamas and undergarments. The backsheet 40 is impervious to liquids (e.g., menses and/or urine). The backsheet 40 preferably comprises a thin, flexible, liquid impervious material.

The backsheet 40 may comprise a woven or nonwoven material, polymeric films such as thermoplastic films of polyethylene or polypropylene, or composite materials such as a film-coated nonwoven material. Preferably, the backsheet 40 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Film Products of Terre Haute, Ind., under the designation XP-39385.

The backsheet 40 is preferably embossed and/or matte finished to provide a more clothlike appearance. Further, the backsheet 40 may permit vapors to escape from the absorbent core 42 (i.e., the backsheet 40 may be breathable) while still preventing exudates from passing through the backsheet 40. Flushable or biodegradable backsheets can also be used, e.g., such as with the pantiliner devices described herein.

The backsheet 40 can be made extensible by performing a mechanical operation, such as pleating, corrugating, or ring rolling the backsheet material. Preferably, however, the backsheet 40 is made extensible by forming it from an elastomeric film such as the film described in U.S. Pat. No. 4,476,180 issued to Wnuk on Oct. 9, 1984. Such a film is obtained from Exxon Chemical Company of Lake Zurich, Ill. as Exxon film EXX-500 (formerly EXX-7).

Another particularly preferred extensible backsheet 40 is an extensible adhesive film Formula #198-338 manufactured by the Findley Adhesives Company of Wauwatosa, Wis. The Findley adhesive film is a liquid impervious film capable of extending 200–300%. The Findley adhesive film is preferred because it is also elastically extensible. The backsheet 40 may comprise extensible laminate structures comprising two or more layers. For instance, a backsheet 40 can comprise a laminate formed of a layer of Findley adhesive film that is covered on both sides by an extensible nonwoven web or by an extensible film. Another suitable backsheet material is nonwoven/film laminate described in U.S. Pat. No. 5,007,906 issued to Osborn Apr. 16, 1991.

The sanitary napkin 20 is also provided with an optional less extensible element 216 positioned between the topsheet 38 and the absorbent core 42. The less extensible element 216 is located approximately in the central region 32 of the sanitary napkin 20. The less extensible element 216 deflects in response to stretching of the rest of the sanitary napkin (and preferably lifts to provide improved body contact).

The less extensible element 216 can generally be any type of component that is less extensible than at least some of the other parts of the main body portion 21 of the sanitary napkin 20. (These other parts of the sanitary napkin refers to those parts of the napkin other than the less extensible barriers. The barriers preferably function independently of the less extensible element.) The less extensible element 216 may be relatively inextensible. In other embodiments, the less extensible element may have a degree of extensibility.

The less extensible element 216 has a body-facing side 216A, a garment-facing side 216B, a pair of longitudinal edges 216C, and a pair of end edges. The structure of the less extensible element 216 is preferably rigid enough to allow bowing or buckling to occur when inwardly-oriented lateral compressive forces are applied to the longitudinal edges 216C of the less extensible element. The less extensible element 216 should preferably not collapse inward (i.e., "squash" like a sponge) without providing any z-direction lift in response to the lateral compressive forces exerted on the sanitary napkin 20 during use. The less extensible element 216 can be in the form of a layer of material, or in some other suitable form. The less extensible element 216 will preferably maintain sufficient rigidity when it is both dry and after it has become wet (such as by body exudates).

The less extensible element 216 may be made from any suitable material. The material should be soft, flexible, and absorbent, but rigid enough to bow or buckle. The less extensible element 216 may be made from many of the basic types of absorbent core materials specified herein. These core materials, however, preferably should not be subjected to any process (such as ring rolling, pleating, corrugating, or slitting) to provide the material with extensibility. FIGS. 1–3 shown an embodiment in which the less extensible element 216 comprises an unslit superabsorbent laminate. The less extensible element 216 is preferably also designed to provide for buckling such as by folding it to create a medial longitudinally-oriented fold line in the same.

The less extensible element 216 may be simply placed on top of the core 42 and held in place by fitting snuggly against the surrounding components of the sanitary napkin 20. In the embodiment shown in FIGS. 1–3, the less extensible element 216 is affixed at a single point 230 on each of its longitudinal side edges.

Figure 4:
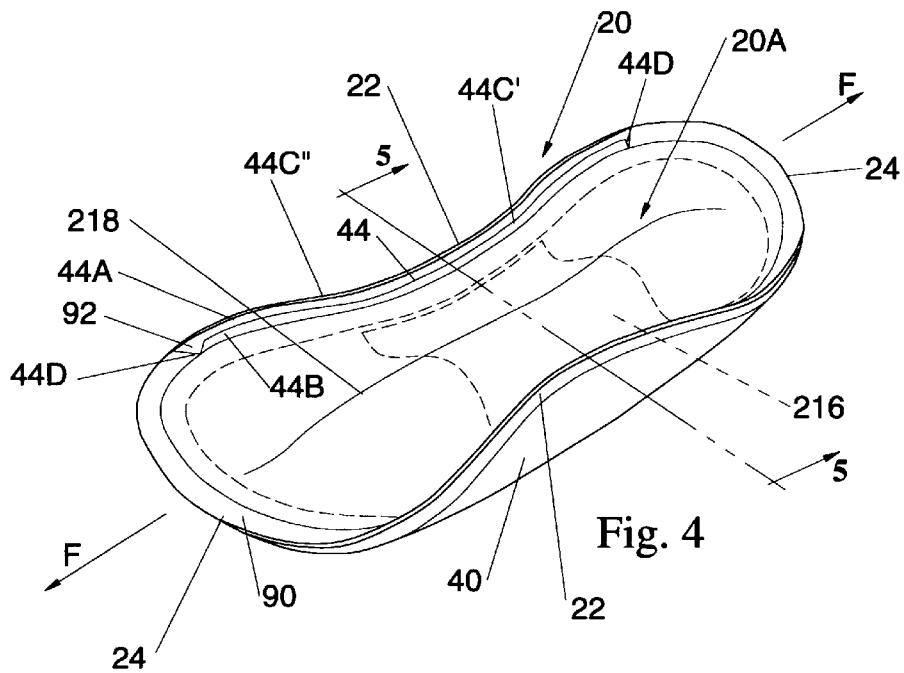
FIG. 4 is a perspective view of the sanitary napkin shown in FIG. 1 after the napkin is extended (with only one barrier shown for simplicity).

When the sanitary napkin 20 is elongated, the central region 32 of the napkin narrows. This causes the less extensible element 216 to bow or buckle and form a ridge 218 (shown in FIGS. 4 and 5) along the longitudinal centerline L of the sanitary napkin 20.

The barriers 44 shown in FIGS. 1–5 comprise narrow strips of material that overlay the topsheet 38. The barriers 44 are preferably placed at least along the longitudinal side edges 22 of the sanitary napkin. The strips 44 each have an outwardly facing side 44A, an inwardly facing side 44B, a pair of edges comprising inner edges 44C', and outer edges 44C", and a pair of ends 44D.

The outer edges 44C" are disposed farther away from the intersection of the longitudinal and transverse centerlines of the sanitary napkin than the inner edges 44C'.

The proximal edges of the barriers are formed by securing the outer edges 44C" and ends 44D of the strips to the topsheet 38 along the perimeter 26 of the sanitary napkin. The inner edges 44C' of the strips are unsecured to the topsheet between the ends 44D of the strips to form free distal edges of the barriers. FIGS. 1 and 2 show a preferred manner of joining the barriers 44 to the topsheet 38. The embodiment shown has barriers 44 with outer edges 44C" that have the same plan view configuration as the edges 22 and 24 of the sanitary napkin. The outer edges 44C" are flush with these side edges. The inner edges 44C' extend inward to slightly over the absorbent core.

The barriers 44 are joined to the topsheet 38 by a barrier seal 92 which is preferably liquid impervious. The barrier seal 92 can be any suitable type of attachment means described herein. Preferably, the barrier seal 92 comprises either an adhesive or heat seal that is applied in approximately the same configuration as the perimeter seam 90 used to secure the topsheet and backsheet (described below).

The barriers 44 shown in FIGS. 1 and 2 have merely one preferred construction. There are numerous possible variations of size and shape of the barriers, and the manner of joining the barriers to the sanitary napkin. The barriers can, for example, be much larger in other embodiments, such as in different types of absorbent articles like diapers. The barriers need not be in the same configuration as the edges of the abosrbent article, nor do they need to be joined flush with the edges of the absorbent article. For example, the barriers may be joined at a proximal edge that is spaced inward from the edges of the absorbent article. The barriers may also, in less preferred embodiments, have distal edges that are joined to the sanitary napkin at some points between the ends of the barriers. Other embodiments are also possible.

The barriers 44 can comprise any suitable liquid impervious or liquid resistant material. The barriers are less extensible than the component (such as the topsheet 38) to which they are attached under the same applied forces. The barriers can be relatively inextensible. Alternatively, the barriers can be extensible but less extensible than the component to which they are attached.

In the preferred embodiment shown in FIGS. 1–3, the barriers comprise an extensible, preferably elastically extensible film such as a film made in accordance to U.S. Pat. No. 4,476,180 issued to Wnuk on Apr. 16, 1991. One such film is elastomeric film EXX-500 (formerly EXX-7) obtained from Exxon Chemical Company of Lake Zurich, Ill. In a particularly preferred embodiment, the barriers 44 comprise strips of such a film 144 that are provided with soft body-facing surfaces to provide increased comfort for the wearer. FIG. 2 shows an example where the strips of film 144 have a soft, preferably highly hydrophobic, nonwoven material 146 laminated to their outwardly-facing sides.

In a particularly preferred embodiment, similar strips can also be affixed along the end edges of the sanitary napkin to form barriers along the entire perimeter of the sanitary napkin. The strips along the side and end edges can be attached to each other to provide a continuous barrier around the entire periphery, or they may be unattached.

Figure 5:
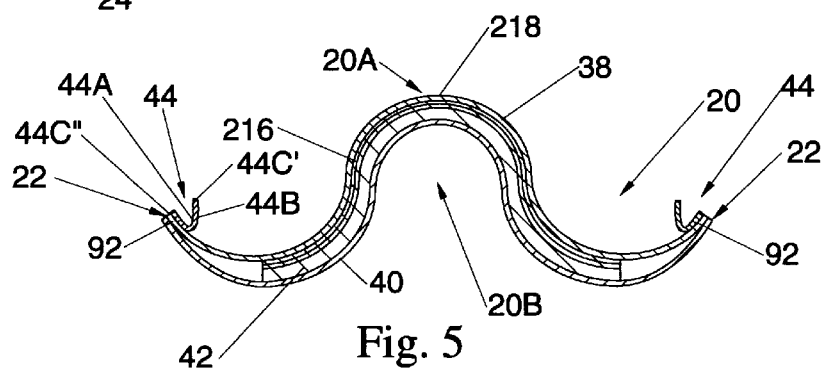
FIG. 5 is a schematic sectional view taken along line 5—5 of the sanitary napkin shown in FIG. 4 (shown with a simplified arrangement of layers and with both barriers in place).

The barriers function in the following manner. If the sanitary napkin is unstretched, the strips 44 lay flat against the topsheet 38. When the sanitary napkin is stretched, the unattached portions of the strips 44 change from a flat disposition to a more upright disposition and form inwardly-facing lips (or gaskets) along the longitudinal edges of the sanitary napkin which serve as barriers to the flow of liquids across the topsheet. The raising of the strips is due to the different amounts the attached and unattached edges of the barrier strips extend. Preferably, as shown in FIG. 5, the barriers and the edge of the sanitary napkin both curl up to form lips and provide a "U"-shaped barrier structure along the edge of the napkin.

The components of the sanitary napkin described above (the topsheet, backsheet, and absorbent core, etc.) can be secured together in any suitable manner that allows the sanitary napkin 20 to extend. In the preferred embodiment shown in FIG. 1, the components of the sanitary napkin 20 are sized so that the edges of the topsheet 38 and backsheet 40 extend outward beyond the edges of the absorbent core 42. The portions of the edges of the topsheet 38 that extend outward beyond the edges of the core 38 are secured to the corresponding portions of the backsheet 40. As shown in FIG. 1, the topsheet 38 is preferably secured to backsheet 40 along liquid impervious seam 90. The seam 90 can be formed by any means commonly used in the art for this purpose, and is preferably formed by adhering the topsheet 38 to the adhesive of the backsheet.

It has been found that such a construction adequately secures the components of the sanitary napkin without securing the faces of the adjacent components to each other. Although, as noted above, it is often preferred to secure some of the components at their faces, as well.

The above is a preferred embodiment for ease of construction. (Other means of uniting the various components can be used.) For instance, the present invention also includes so-called "tube" products. In these products, a liquid pervious cover material (such as topsheet material) can be wrapped completely around the absorbent core and the backsheet, and then the components can be secured together. In alternative arrangements, the topsheet could be wrapped around the core, and the wrapped core could be placed on and secured to the backsheet.

FIG. 3 shows that the garment surface 20B of the sanitary napkin may be provided with a fastener, such as pressure sensitive adhesive 50, to secure the sanitary napkin 20 to the crotch of a panty. The adhesive can be applied in other suitable configurations. The adhesive fastener 50 can be extensible, inextensible, or it can be applied so that some portions of the pattern are extensible and some portions of inextensible.

If the adhesive is extensible, it preferably extends approximately the same amounts as the sanitary napkin as set forth in FIG. 7. Suitable extensible adhesives include extensible adhesives, per se, and extensible adhesive/barrier film combinations. Any extensible adhesives known in the art can be used. Suitable extensible adhesive/barrier film combinations include, but are not limited to non-extensible adhesive used on an extensible barrier film material; elastically stretchable adhesive films such as Findley adhesive 198-338; or spray adhesives such as 3M adhesive 1442 on a low modulus elastic film.

Suitable inextensible adhesives may be those adhesives specified as 0.6 mil pass available from Century Adhesive as product number A305-4, or from Anchor Continental, Inc., 3 Sigma Division, of Covington, Ohio, and Fuller H-2238ZP manufactured by the H.B. Fuller Co. Suitable inextensible adhesive fasteners are described in greater detail in U.S. Pat. No. 4,917,697.

The adhesive fastener 50 is preferably covered with a release liner (or cover strip) 52. Any commercially available release liner can be used. In one preferred embodiment, the release liner can be replaced by a wrapper that provides both an individually packaged sanitary napkin and a container for disposing the sanitary napkin after use, such as is described in U.S. Pat. No. 4,556,146 issued to Swanson, et al. on Dec. 3, 1985.

The fasteners have be initially described in terms of adhesives for simplicity of description. The types of fasteners are not limited to adhesives, however. Preferred fasteners include but are not limited to adhesive fastening means, such as pressure sensitive adhesives, mechanical fasteners and combinations of adhesives and mechanical fasteners. The sanitary napkin may also be provided with optional polyethylene end guards 140.

The following Example further illustrates the practice of the present invention. The following Example, however, is not intended to limit the scope of the absorbent articles encompassed herein.

EXAMPLE

The components of the sanitary napkin are obtained. The topsheet 38 is made in accordance with U.S. Pat. No. 4,463,045 and ring rolled to provide it with extensibility. A superabsorbent material containment layer is obtained in the form of a single ply of "BOUNTY" tissue 200 taken from the Yankee dryer without removal of the crepe. The core is an absorbent gelling material (AGM) laminate which is slitted over its entire length for longitudinal extensibility. The backsheet is a laminate of Findley 198-338 adhesive and a nonwoven fabric. The nonwoven fabric is Celanese nonwoven fabric t-138 obtained from Veratec of Walpole, Mass. The nonwoven material is laminated to the Findley adhesive film so that the laminate will stretch in the longitudinal direction (which will be perpendicular to the orientation of the fibers in the nonwoven). The nonwoven material will be on the outside of the finished product.

The assembly of the product is as follows. Cut the ring rolled topsheet to size. Bond the creped "BOUNTY" tissue to the topsheet by applying Findley H2031 adhesive to the topsheet in spiral pattern at 0.005 g/in$^2$. Cover the end regions of the garment-facing side of the core with pieces of creped BOUNTY tissue. Place the absorbent core on top of the backsheet. Place a 2½"×2⅝ piece of unslit AGM laminate over the center region of the body-facing side of the core. Adhere the piece of AGM laminate at the center of its longitudinal edges to the edges of the backsheet with adhesive. Place the topsheet and creped tissue laminate over the core. Secure the components and smooth at the edges. Roll the edges to seal the edges. Trim to the final shape. Adhere a piece of EX-500 along the side edges of the pad by a heat seal so that the distal edge extends 2 mm over the topsheet toward the center of the core in the narrowest center region of the pad and 5 mm at the widest end regions of the pad. Apply the Fuller HL 2238 panty fastening adhesive (PFA) adhesive to the garment-facing surface of the product in a spiral in the pattern shown in FIG. 3. Spray the topsheet with 0.01 grams Pegosperse 200 ML surfactant available from Lonza, Inc. Williamsport, Pa.

Figure 8:
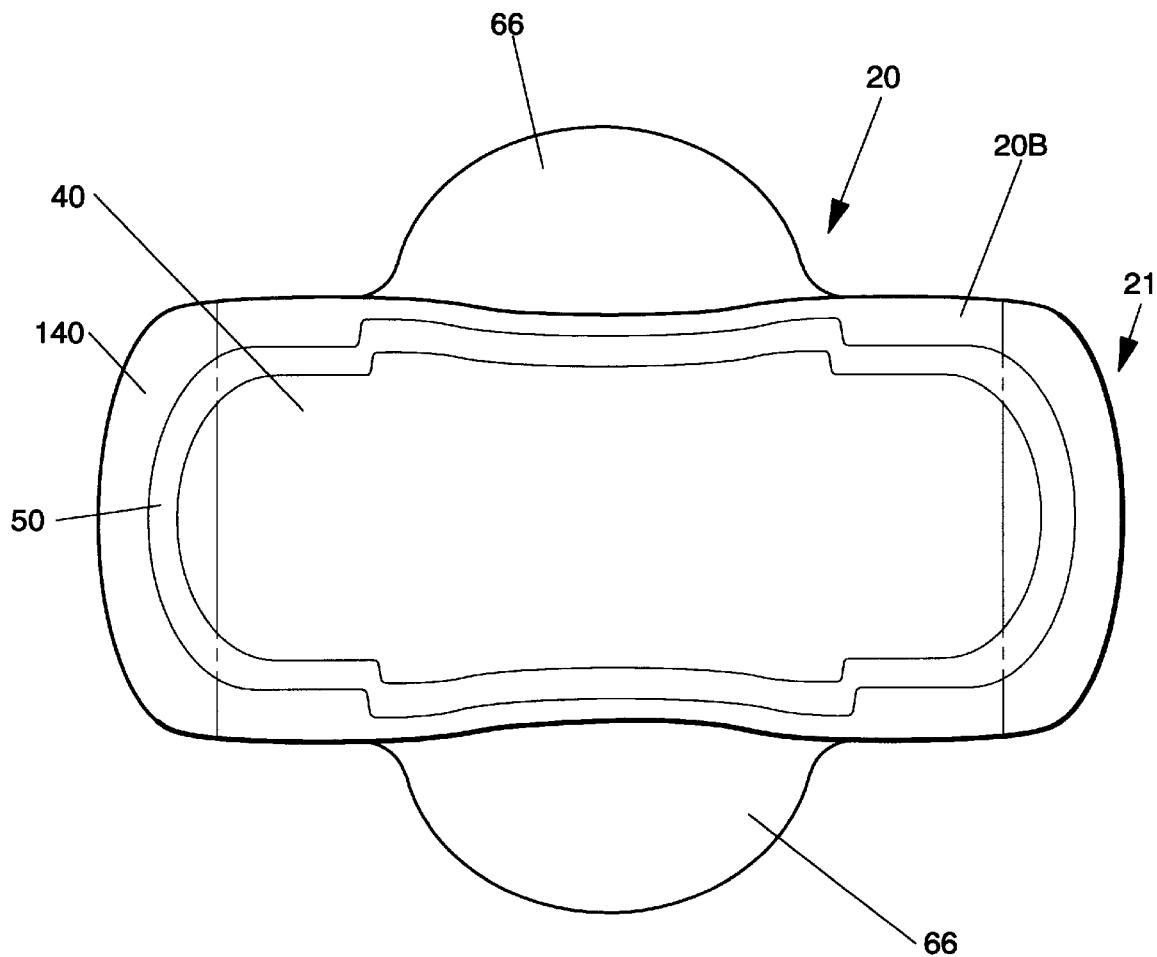
FIG. 8 is a bottom plan veiw of a sanitary napkin according to the present invention which is provided with a pair of side flaps.

While a preferred sanitary napkin has been described, numerous other sanitary napkin embodiments are disclosed in the literature. The sanitary napkin could be provided with some or all of the components or features described therein. The sanitary napkin 20 may as shown in FIG. 8, for example, also be provided with a pair of flaps 66, each of which are adjacent to and extend laterally outward from a side edge of the main body portion 21 of the sanitary napkin. (The main body portion is the portion of the sanitary napkin without the flaps.) A number of sanitary napkins having flaps suitable or adaptable for use with the sanitary napkin 20 of the present invention are known. Such flaps are disclosed in U.S. Pat. No. 4,285,343 entitled "Sanitary Napkin", issued to McNair on Aug. 25, 1981; U.S. Pat. No. 4,589,876 entitled "Sanitary Napkin", issued to Van Tilburg on May 20, 1986; U.S. Pat. No. 4,608,047 entitled "Sanitary Napkin Attachment Means", issued to Mattingly on Aug. 26, 1986; U.S. Pat. No. 4,687,478 entitled "Shaped Sanitary Napkin With Flaps", issued to Van Tilburg on Aug. 18, 1987; and in Reexamination Patent B14,589,876 issued Apr. 27, 1993. Some particularly preferred types of flaps are described in the following U.S. patent applications: Ser. No. 07/769,891 entitled "Absorbent Article Having Flaps and Zones of Differential Extensibility" filed in the name of Lavash, et al. on Oct. 1, 1991 (PCT Publication No. WO 93/06805, published Apr. 15, 1993); and in Ser. No. 07/906,593 entitled "Absorbent Article Having Unitary Release Material" filed in the name of Lavash, et al. and Ser. No. 07/906,629 entitled "Absorbent Article Having Tucked Flaps" filed in the name of Osborn, et al., both filed Jun. 30, 1992.

Further, it should also be understood PCT Publication Nos. WO 93/01785 and WO 93/01786 and all the test methods set forth therein are incorporated by reference herein. In this regard, the procedure for measuring the longitudinal extensibility of a one inch (2.5 cm) strip can be modified by cutting the strip not only through the longitudinal centerline, but parallel to the longitudinal centerline so that the entire width of the sample contains at least one of the absorbent components of the absorbent article. The sample should not be cut so close to the longitudinal side edges of the absorbent article, however, that it contains any side elastic features. If any of the samples thus measured are within the range set forth in the claims, then the absorbent article falls within the scope of the claims.

The terms "panty liner" or "pantiliner" refer to absorbent articles that are less bulky than sanitary napkins which are generally worn by women between their menstrual periods. An example of an absorbent article in the form of a pantiliner is disclosed in U.S. Pat. No. 4,738,676 entitled "Pantiliner" issued to Osborn on Apr. 19, 1988.

The term "incontinence article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinent articles that can be provided with the components described herein are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. patent application Ser. Nos. 07/637,090 and 07/637,571 filed respectively by Noel, et al. and Feist, et al. on Jan. 3, 1991 (PCT Publication Nos. WO 92/11830 and WO 92/11831, both published Jul. 23, 1992).

The focus of the present invention is on absorbent articles that are intended to be worn in the crotch region of the wearer's undergarments. However, the features of the present invention could also be used in absorbent articles such as diapers. Diapers are absorbent articles worn by infants and incontinent persons that are fastened about the waist of the wearer. Suitable diapers that can be provided with the components described herein are disclosed in U.S. Pat. No. 3,860,003 issued to Buell on Jan. 14, 1975, and U.S. Pat. No. 5,151,092 issued to Buell, et al. on Sep. 29, 1992.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent article having a longitudinal centerline extending in a longitudinal direction, a transverse centerline extending in a transverse direction, a pair of longitudinal side edges and a pair of end edges which form the periphery of the absorbent article, said absorbent article comprising:

a liquid pervious topsheet;

a liquid impervious backsheet joined to said topsheet;

an absorbent core positioned between said topsheet and said backsheet; and a barrier adjacent at least one of the longitudinal side edges of the absorbent article, said barrier having an inner edge, an outer edge, and a pair of ends, wherein said outer edge and ends of said barrier are joined to said topsheet and at least a portion of said inner edges of said barrier being unattached to said topsheet between said ends; and wherein at least said topsheet is extensible and said barrier is less extensible than said topsheet so that upon extension of said topsheet, said barrier moves to a more upright disposition to form a lip that serves as a barrier to the flow of liquids.

2. The absorbent article of claim 1 wherein said topsheet is extensible in the longitudinal direction.

3. The absorbent article of claim 1 having two barriers, one adjacent each longitudinal side edge.

4. The absorbent article of claim 3 further comprising a barrier adjacent each of the end edges.

5. The absorbent article of claim 1 wherein said backsheet and said absorbent core are also extensible.

6. The absorbent article of claim 1 wherein said barrier comprises a liquid impervious film.

7. The absorbent article of claim 6 further comprising a soft material covering said liquid impervious film.

8. The absorbent article of claim 1 having a first end region, a second end region and a central region disposed between said first and second end regions, wherein the central region of the absorbent article is narrower than the end regions.

9. The absorbent article of claim 8 having an hour glass shape.

10. The absorbent article of claim 8 having a dog bone shape.

11. The absorbent article of claims 1 or 8 having a main body portion comprised of at least portions of said topsheet, backsheet, and absorbent core, said main body portion having said pair of longitudinal side edges and said pair of end edges further comprising a pair of flaps extending outward from the longitudinal edges of said main body portion of said absorbent article.

* * * * *